United States Patent [19]

Burger et al.

[11] Patent Number: 4,603,142
[45] Date of Patent: Jul. 29, 1986

[54] CHOLESTEROL LOWERING METHOD OF USE

[75] Inventors: Warren C. Burger, Mt. Horeb; Asaf A. Qureshi; Charles E. Elson, both of Madison, all of Wis.

[73] Assignee: Wisconsin Alumni Research Foundation, Madison, Wis.

[21] Appl. No.: 616,478

[22] Filed: Jun. 1, 1984

[51] Int. Cl.$^4$ .................. A61K 31/35; A61K 31/355; C07D 311/04; C07D 311/74; C07D 311/76
[52] U.S. Cl. .................................... 514/456; 514/458
[58] Field of Search ................ 424/283, 284; 549/408; 514/456, 458

[56] References Cited

U.S. PATENT DOCUMENTS

| | | | |
|---|---|---|---|
| 3,317,564 | 5/1967 | Rüegg et al. | 549/408 |
| 3,869,477 | 3/1975 | Shindo | 424/284 |
| 3,883,565 | 5/1975 | Cunningham | 424/284 |
| 4,034,083 | 7/1977 | Mattson | 424/284 |
| 4,088,778 | 5/1978 | Igarshi et al. | 424/284 |
| 4,122,094 | 10/1978 | Woziwodzky | 260/345.5 |
| 4,285,951 | 8/1981 | Hoefle | 424/263 |
| 4,351,950 | 9/1982 | Sircar | 560/62 |

FOREIGN PATENT DOCUMENTS

| | | | |
|---|---|---|---|
| 1365222 | 5/1964 | France | 549/408 |
| 1405507 | 5/1965 | France | 549/408 |
| 59886 | 4/1982 | Japan | 549/408 |
| 99475 | 6/1983 | Japan | 549/408 |
| 5178 | 1/1984 | Japan | 549/408 |
| 5179 | 1/1984 | Japan | 549/408 |
| 2090836 | 7/1982 | United Kingdom | 549/408 |
| 2117381 | 10/1983 | United Kingdom | 549/408 |

OTHER PUBLICATIONS

Chemical Abstracts, vol. 83 (1975), #97026n; Cunningham-Mulholland.
Chemical Abstracts; vol. 88 (1978), #88024m; Leonhardt.
Chemical Abstracts, vol. 99 (1983), #93758k, Teijin.
Kritchevsky, D. Dietary Fiber and Other Dietary Factors in Hypercholesteremia. Am. J. Clin. Nutr. 30:979-984 (1977).
Chen, W. J. L., Anderson, J. W., and Gould M. R. Effect of Oat Bran, Oat Gum and Pectin on Lipid Metabolism of Cholesterol-Fed Rats. Nutr. Rep. Inter. 24: 1093-1098 (1981).
Burger, W. C., Quershi, A. A., Prentice, N. and Elson, C. E. Effects of Different Fractions of the Barley Kernel on the Hepatic Lipid Metabolism of Chickens, Lipids. 17(12) 956-963 (1982).
Qureshi, A. A., Burger, W. C., Prentice, N., Bird, H. R. and Sunde, M. L. Regulation of Lipid Metabolism in Chicken Liver by Dietary Cereals, J. Nutr. 110:338-393 (1980).
Qureshi, A. A., Abuirmeileh, N., Burger, W. C., Din, Z. A., and Elson, C. E. Effect of AMO 1618 on Cholesterol and Fatty Acid Metabolism in Chickens and Rats, Atherosclerosis, 46, 203-216 (1983).
Kirby, R. W., Anderson, J. W., Sieling, B., Rees, E. D., Chen, W. J. L., Miller, R. E., and Kay, R. M. Oat-Bran Intake Selectively Lowers Serum Low-Density Lipoprotein Concentrations of Hypercholesterolemic Men. Am. J. Clin. Nutr. 34:824-829 (1981).
Fraser, G. E., Jacobs, D. R. Jr., Anderson, J. T., Foster, N., Palta, M., and Blackburn, H. The Effect of Various Vegetable Supplements on Serum Cholesterol, Am. J. Clin. Nutr. 34:1272-1277 (1981).
Akiba, Y. and Matsumoto, T. Effects of Several Types of Dietary Fibers on Lipid Content in Liver and Plasma, Nutrient Retentions and Plasma Transaminase Activities in Forced-Fed Growing Chicks, J. Nutr. 110:1112-1121 (1980).
Fisher, H. and Griminger, P. Cholesterol-Lowering Effects of Certain Grains of Oat Fractions in Chick, Proc. Soc. Exp. Biol. Med. 126:108-111 (1967).
Burger, W. S., Quershi, A. A. and Prentice N. Dietary Barley as a Regulator of Fatty Acid Metabolism in the Chicken, Rat and Swine, Abstract Symposium, Jul. 22-29th 1981, Ediburgh, Scotland.
Barley Components Reduce Cholesterol and Enhance Animal Growth, Research News U.S. Dept. of Agriculture, Jul. 13, 1981.
Substance Found in Barley Reduces Cholesterol Levels, Research Division Science Report, College of Agriculture and Life Sciences University of Wisconsin-Madison, Apr. 15, 1981.
Din, Z. A., Burger, W. C., Ahmad, Y. and Quershi, A. A. The Structure of Cholesterol Inhibitor I Isolated from High-Protein Barley Flour (HPBF) and its Effects on Cholesterogenesis in Chickens, Abstract Published May 1, 1984, American Soc. of Biological Chemists.

*Primary Examiner*—Leonard Schenkman
*Assistant Examiner*—Joseph A. Lipovsky
*Attorney, Agent, or Firm*—Quarles & Brady

[57] ABSTRACT

A method of lowering cholesterol comprises administering to an animal safe and effective amounts of d-α-tocotrienol. A method of extracting d-α-tocotrienol from natural sources and pharmaceutical compositions containing d-α-tocotrienol are also disclosed.

4 Claims, No Drawings

CHOLESTEROL LOWERING METHOD OF USE

FIELD OF THE INVENTION

The present invention relates to novel pharmaceutical compositions which can be used to lower blood cholesterol. It also relates to a method of use employing those compositions.

BACKGROUND OF THE INVENTION

It is generally recognized that high blood cholesterol levels are significant risk factors in cardiovascular disease which comprises a major health care problem today. Studies have demonstrated that with very few exceptions, populations which consume large quantities of saturated fat and cholesterol have relatively high concentrations of serum cholesterol and a high mortality rate from coronary heart disease. While it is recognized that there are other factors that can also contribute to the development of cardiovascular disease, there is increasing evidence that a causal relationship exists between the concentration of serum cholesterol and the accumulation of undesirable amounts of cholesterol in various parts of the circulatory system in coronary disease. Recent studies have indicated that it is total and low density lipoprotein cholesterol which should be lowered and that it may actually be beneficial to have an elevated high density lipoprotein cholesterol level.

It obviously would be desirable to have pharmaceutical compositions which lower blood cholesterol and low density lipoprotein concentrations in the blood without adversely affecting high density lipoprotein levels and without undesirable side effects.

SUMMARY OF THE INVENTION

It is the primary object of the present invention to disclose novel pharmaceutical compositions which lower blood cholesterol and low density lipoprotein concentrations in the blood.

The pharmaceutical compositions of the present invention contain as the active ingredient a compound having the following formula:

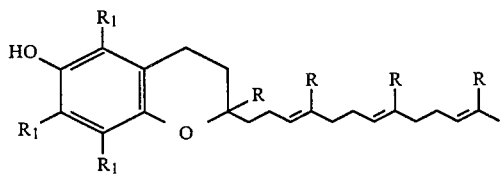

in which R and $R_1$ are the same or different and are lower alkyls of 1 to 4 carbon atoms and preferably methyl. In the novel compositions, the active ingredient may be combined with conventional pharmaceutical diluents and flavoring agents to form pharmaceutical compositions suitable for oral or parenteral administration.

In the method of the present invention, the active ingredient in the form of pharmaceutical compositions is administered in a safe and effective amount to lower the animal's blood total and low density lipoprotein cholesterol levels.

These and other advantages and objects of the invention will be apparent to those skilled in the art.

DESCRIPTION OF THE PREFERRED EMBODIMENT

The preferred compositions of the present invention are those which contain the compound d-α-tocotrienol as the active ingredient. The compound d-α-tocotrienol may be represented by the following formula:

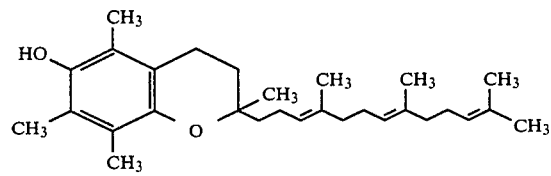

The compositions may take the form of tablets, capsules emulsions, suspensions and powders for oral administration and sterile solutions or emulsions for parenteral administration.

In the preferred method of the present invention, d-α-tocotrienol in the form of a capsule or tablet is orally administered in a safe and effective amount to an animal to lower the animal's blood total and low density lipoprotein cholesterol levels.

We have discovered that d-α-tocotrienol (2, 5, 7, 8-tetramethyl-2 (4, 8, 12-trimethyltrideca-3, 7, 11-trienyl)chroman-6-ol) is an inhibitor of cholesterol biosynthesis and is present in the nonpolar fraction (petroleum ether solubles) of commercial high-protein barely flour (HPBF).

It had previously been observed that in some areas of Asia humans consuming barley as the major dietary cereal were alleged to experience a very low instance of cardiovascular diseases. Since such diseases were frequently associated with abnormally high concentrations of blood cholesterol, particularly in the form of very low density lipoproteins, it was suspected that the consumption of barley had something to do with the low cholesterol levels. Initially, it was felt that dietary fiber, which has been suggested as being directly related to decreased blood cholesterol levels, might possibly be binding or sequestering the normal degradation products of cholesterol, the bile acids, in the gut, thus enhancing cholesterol degradation. However, as part of a program concerned with the nutritional properties of barley, we studied the lipid metabolism in the livers of young chickens which had been fed wheat, barley, oats, rye, and corn as the major energy source. We discovered that cholesterol biosynthesis was markedly suppressed, particularly by barley. Further studies indicated that one cholesterol inhibiting factor that was present in barley was d-α-tocotrienol.

We have isolated pure d-α-tocotrienol from barley. Our animal tests have demonstrated that even in low concentrations the compound controls the biosynthesis of cholesterol and results in lower concentrations of total and low density lipoprotein cholesterol in test animals. We also have found that the compound has no significant effect on the desirable high density lipoprotein cholesterol levels and no undesirable side effects. In addition to being extractable from natural sources, including barley and lemon grass oil, d-α-tocotrienol can be synthesized using available technology similar to that which has been used in the synthesis of Vitamin E and more recently as described by S. Urano et al. (J. Chem. Pharm. Bull. 31, 4341 (1983)).

The tocotrienols are widely distributed in the plant kingdom and differ from their counterpart tocopherols (Vitamin E) only in that the tocotrienols have three double bonds in the isoprenoid sidechain. The sidechain appears to be essential for the observed inhibition of cholesterol biosynthesis because Vitamin E does not cause a similar lowering of cholesterol. The effect of Vitamin E on lipoprotein cholesterol distribution has been studied and was reported by W. J. Herrman in the article entitled The Effect of Vitamin E on Lipoprotein Cholesterol Distribution, in New York Academy of Science 363:467-72 (1982). Most of the published work on the lowering of cholesterol levels in animals has been concerned with the effects of plant fibers and gums, although some proprietary materials of fungal or synthetic origin have been marketed.

A description of the experimental work which led to the isolation of d-α-tocotrienol and the determination of its cholesterol lowering activity is described herein.

EXPERIMENTAL WORK AND RESULTS

Chicks fed a diet based on barley, wheat, oats or rye exhibited, compared to chicks fed a standard corn-soy diet, inferior growth, smaller livers and excreted sticky feces as well. These responses were attributed to the presence in the small grains of relatively high concentrations of beta-D-glucans and pentosans. A long-standing interest in lipid metabolism prompted us to examine certain lipogenic and cholesterolgenic enzymes in the tissues of these birds. Methods used for handling blood samples, preparing subcellular fractions of liver and assay procedures for beta-hydroxy-beta-methylglutaryl coenzyme A (HMG Co-A) reductase, fatty acid synthetase (FAS), plasma cholesterol and triglycerides and the statistical treatment of the data have been described [Qureshi AA et al. (1980): Regulation of lipid metabolism in chicken livers by dietary cereals, J Nutr 110:388-393].

Levels of HMG Co-A reductase in the livers of the birds fed barley, oats and rye were disproportionately low relative both to the controls and to body size. The HMG Co-A reductase activity relative to body and liver weight was comparable between birds fed the standard and wheat-based diets, even though the latter had lower body size and liver weights. Barley was particularly effective in limiting cholesterol biosynthesis (HMG Co-A reductase) with only 21% of the control activity. Plasma cholesterol concentrations reflected the lower rate of synthesis; the barley-fed birds had only 55% of the control concentration, while concentrations in birds fed oats, rye and wheat range from 68-76% of the control. Although cholesterol biosynthesis was depressed, lipogenesis was highly stimulated. FAS determinations suggested that barley increased lipogenesis 5-fold, whereas the other grains produced smaller but significant increases. The sharp difference in response of the cholesterol and fatty acid biosynthetic systems suggested that at least two active substances were present in the small grains.

A comparison between corn and barley diets using 21-day-old female rats showed the latter effected a better growth rate and a 50% reduction in HMG Co-A reductase activity. When compared to a commercial chow diet, barley supported a 20% lower weight gain and HMG Co-A reductase was reduced by 80%. In 5-month-old Yorkshire and Hampshire gilts, 82% corn and 82% barley diets produced about equal weight gains but the latter diet produced 19-25% reductions in HMG Co-A reductase activity in liver, adipose, intestine, lung and muscle tissues and 17% less cholesterol in plasma and muscle [Qureshi AA et al. (1982): Effects of cereals and culture filtrate of *Trichoderma viride* on lipid metabolism of swine, *Lipids* 17:924-934].

Feeding trials with chickens of different ages were run to determine the location and distribution of the active substance(s) within the barley kernel. Three fractions, barley pearlings (16.4% protein), high-protein barley flour (19.4% protein, HPBF) and pearled-barley (11.1% protein) obtained during commercial pearling operations were fed in the same manner as the intact grains, corn (10.9% protein) and barley (12.8% protein). Data obtained when 1-day-old chicks were fed diets containing these fractions as the major ingredient for four weeks revealed various growth responses with barley being about equal to corn, pearled-barley somewhat less effective at 83% of the control and pearlings containing HPBF and HPBF by itself being very poor in this respect. All three barley fractions produced strong suppression of HMG Co-A reductase activity, but only the HPBF was equal to the whole barley in this aspect. Plasma cholesterol and triglyceride levels were suppressed and enhanced, respectively, by barley and the three fractions. The suppressant of HMG Co-A reductase appeared to be concentrated in the outer layers of the starchy endosperm (the HPBF). Since the pearlings also contained HPBF, it is assumed that the suppressor activity obtained with the pearlings was due in large measure to the HPBF contaminant. It should be recognized, though, that pearled barley freed of most of the outer layer of the starchy endosperm also contained suppressor activity.

In another experiment, White Leghorn chickens, 12-weeks of age were pair-fed isonitrogenous HPBF-based diets for 3 weeks. Gains in weight were comparable between the HPBF and cornbased dietary groups. HMG Co-A reductase activity was 72% of the control and plasma cholesterol 84%, whereas FAS activity was 132% of the control.

The extremely poor growth response to HPBF diets was investigated further. When chicks 4-weeks of age or older were fed HPBF diets, weight gains approximating those obtained with corn were recorded. It thus appears that only the very young chicks were incapable of utilizing HPBF as the major dietary component. Poor growth observed in the young birds is likely related to a transient inability to utilize beta-D-glucans and/or pentosans.

The suppression of cholesterol production by HPBF also was more pronounced in very young birds. This suppression was not due to the lower growth rate because a significant suppression of cholesterol production was present in older birds whose growth rate was comparable to corn-fed controls. More significantly, an enhanced growth rate was observed in young birds when 5-20% HPBR was fed. In these experiments, 5, 10, 15 or 20% HPBF was added to the diet in place of corn. Significant positive correlations were obtained between the level of dietary HPBF and FAS activities, and negative correlations were calculated between level of HPBF and HMG Co-A reductase activity [Burger WC et al. (1982): Effects of different fractions of the barley kernel on the hepatic lipid metabolism of chickens, *Lipids* 17:956-963].

In still another experiment, White Leghorn restricted ovulator (RO) hens were fed control or diets containing 20% HPBF. The RO hen has a sexed-linked genetic defect in egg laying which results in hyperlipidemia. Compared to normal hens, mature RO hens have a 17% reduction in hepatic HMG Co-A reductase activity, presumably due to the feedback suppression mediated by the high level of circulating cholesterol. Hepatic HMG Co-A reductase activity was decreased another 13% by the feeding of the 20% HPBF diet [Qureshi AA et al. (1983): Regulation of lipid metabolism in restricted ovulator chicken by dietary supplementation with HPBF and culture filtrate, *Nutr Reports Inter* 27:87–95].

These observations prompted us to use a sequential extraction with solvents of increasing polarity as a preliminary step in the purification of the active agents in HPBF. Extraction was accomplished by sequentially extracting the flour with petroleum ether, ethyl acetate and methanol. Two hundred grams of HPBF were extracted with three 200 ml portions of each solvent, the portions were pooled and evaporated to dryness. The solids were weighed and then added to the corn-based control diet at levels equivalent to 20% HPBF and fed to chickens. Distributed among the solvent fractions were components which influenced weight gain, HMG Co-A reductase, cholesterol 7-alpha-hydroxylase and FAS activities, and serum concentrations of cholesterol and triglycerides. Feeding either 20% HPBF or solvent fractions of HPBF significantly lowered hepatic HMG Co-A reductase, cholesterol 7-alpha-hydroxylase activities and serum cholesterol concentrations. The components extracted with petroleum ether significantly increased weight gain and suppressed FAS activity, whereas components extracted by the more polar solvents (ethyl acetate and methanol) tended to decrease weight gain and significantly increase FAS activity. Significantly lower and higher concentrations of triglycerides were recorded for the serum of birds fed the non-polar (petroleum ether) and polar (methanol) extracts, respectively [Qureshi AA et al. (1982): Suppression of cholesterol biosynthesis by dietary high protein barley flour, *Am J Clin Nutr* 35:855].

In other experiments, the fractions obtained by serial extraction of HPBF with solvents of increasing polarity were fed at levels equivalent to 20% HPBF in a corn-based diet to female White Leghorn chickens for three weeks. The petroleum ether-soluble fraction produced three effects: an increase in body weight gain (23%), a strong suppression of HMG Co-A reductase ($-36\%$), and FAS ($-40\%$) accompanied by decreases in serum triglycerides ($-9\%$) and cholesterol levels ($-23\%$). The methanol-soluble fraction produced a significant suppression of HMG Co-A reductase ($-49\%$) and serum cholesterol level ($-29\%$), and an increase in FAS activity ($+95\%$).

In still another type of experiment, diets containing the various dried solvent-extracted materials at concentrations equivalent to 20% HPBF were fed to 7-week-old chickens for four weeks. The results reported above were confirmed. Petroleum ether solubles produced a 20% increase in body weight gain, a strong suppression of HMG Co-A reductase and a suppression of FAS. This effect on FAS was apparently masked in trials with HPBF or intact barley, as we did not observe any suppression of this enzyme under those dietary conditions. The pooled materials in the methanol-soluble fraction produced a significant ($p \geq 0.01$), but less pronounced suppression of HMG Co-A reductase and stimulated FAS activity as previously noted. In this experiment, we noted that the reduction in plasma total cholesterol concentration was due only to a lowering of the cholesterol transported in the low density lipoprotein (LDL-chol) fraction of the plasma lipoproteins. Again, factors influencing this parameter were equally divided between the polar and nonpolar fractions [Burger WC et al. (1984): Suppression of cholesterol biosynethesis by constituents of barley kernel, *Atherosclerosis* 51:75–87].

The serial extraction of HPBF revealed the presence of two effectors of lipogenic activity. One effector was petroleum ether-soluble and suppressed FAS activity; the second extracted with methanol (polar solvents) following the removal of the first effector markedly increased FAS activity. The results described are noteworthy in two respects: the variety and magnitude of the biochemical effects associated with dietary barley or, more specifically, HPBF, and the lack of any precedent for such materials from cereal grains acting at the cellular level. The results indicate that there are at least two substances, one polar and one nonpolar, in HPBF capable of producing relatively strong suppression of the rate-limiting enzyme for cholesterol biosynthesis in liver, the primary site of cholesterol production in humans as well as chickens.

These observed effects on lipogensis and cholesterogenesis could be attributed to the chemical constituents of HPBF, but clearly could not be attributed to the water insoluble plant fibers because they were not present in the latter feeding trials. Moreover, these effects were also obtained in vitro using isolated hepatocytes from chickens and rats. A concentration-dependent inhibition of hepatic HMG Co-A reductase and FAS activities in isolated hepatocytes was observed at 15 minutes [Burger WC et al. (1983): Suppression of cholesterogenesis in isolated hepatocytes by constituents of high protein barley flour, *Fed. Proc.* 42:1973 (Abstr.)]. Conditions for the in vitro evaluation of the solvent extracts have been described [Qureshi AA et al. (1983): Inhibition of cholesterol and fatty acid biosynthesis in liver enzymes and chicken hepatocytes by polar fractions of garlic, *Lipids* 18:343–348].

Our next effort was to purify the cholesterol inhibitor present in the petroleum ether fraction of the HPBF. Separation of the components of this fraction was achieved using semipreparative high-performance liquid chromatography (HPLC), using Beckman Ultrasphere C18, IP (25 cm×10 mm I.D. column, 10 micron particle size). A 50 microliter aliquot of the petroleum ether solubles was placed on the column and eluted with methanol at a flow rate of 1 ml/minute at 700 psi. The detecting wavelength was 200 nm. Ten major peaks were collected. Fractions corresponding to these peaks were checked in vitro for their capacity to suppress HMG Co-A reductase activity in isolated hepatocytes. Fractions five (cholesterol inhibitor I) and nine (cholesterol inhibitor II) from the column produced significant inhibition of HMG Co-A reductase. Cholesterol inhibitor I (frac. 5) and cholesterol inhibitor II (frac. 9) produced significant increase and decrease in the activities of FAS, respectively. These fractions were then purified by analytical thin-layer chromatography (TLC) on silica gel G-plates 0.5 mm, in a solvent system consisting of 95% benzene plus 5% ethyl alcohol. These purified components eluted from the TLC plate were subjected to HPLC and each showed one peak on rechromatography.

For large scale preparation of these compounds, 10 grams of the petroleum ether soluble fraction of HPBF were dissolved in 10 ml petroleum ether and applied to a 90×3.5 cm silicic acid column (Bio-Silica, 100-200 mesh). The column was washed with 2,500 ml petroleum ether followed by stepwise elution with increasing amounts of ether in petroleum ether. Fraction 8 of the column corresponded to HPLC fraction 5. The purified compound was tested for dose response effect (2.5 to 20 ppm) as shown in Table 1. A concentration-dependent suppression of HMG Co-A reductase activity and enhancement of FAS activity was noted within this range. Serum total and LDL cholesterol levels also fell in a dose-dependent response. The level of cholesterol transported in the high-density lipoprotein fraction (HDL) was not influenced by cholesterol inhibitor I (Table 1). In a companion experiment, using the same control birds, the effect of cholesterol inhibitor I at 5 ppm is compared to the effect of the petroleum ether solubles of HPBF at 20% equivalent on weight gain, HMG Co-A reductase and FAS activities, serum cholesterol and serum triglyceride levels (Table 2). The petroleum ether soluble fraction of HPBF again stimulated weight gain and suppressed FAS activity, whereas cholesterol inhibitor I at 5 ppm had no influence on weight gain and increased FAS activity. Serum triglyceride levels reflected the influence of the diet on FAS activity. Serum total cholesterol was significantly lowered by both treatments, whereas HDL cholesterol was not affected. Cholesterol inhibitor I was a more powerful suppressor of LDL cholesterol (Table 2).

Cholesterol inhibitor I was re-chromatographed by HPLC and the UV absorption spectrum obtained. Maximum absorption occurred at 292 nm. This purified fraction was used for high resolution mass spectrometric analysis. Several scans were made using ionization temperatures from 90-180 degrees Centigrade to increase the possibility of detecting impurities. The high resolution mass spectrometric analysis and measurements of different peaks gave a molecular ion peak at m/e 424 and main peaks at m/e 385, 205 and 165 corresponding to $C_{29}H_{44}O_2$ (molecular formula) $C_{25}H_{36}O_2$, $C_{13}H_{17}O_2$ and $C_{10}H_{13}O_2$ moieties, respectively, which are characteristic fragmentation moieties for d-alpha-tocotrienol. Lemon grass oil is a rich source of d-alpha-tocotrienol. This product and cholesterol inhibitor I at 20 ppm were compared with the petroleum ether soluble fraction of HPBF (20% equivalent HPBF) in a group of older male White Leghorn chickens (Table 3). The results shown on Table 3 confirm those previously recorded for petroleum ether solubles of HPBF and cholestrol inhibitor I. In a final experiment, the effects of cholestrol inhibitor I and lemon grass oil on hepatocyte HMG Co-A reductase and FAS activities were tested. Both components tested in the concentration range 5-100 microgram/ml, produced a concentration-dependent suppression of HMG Co-A reductase and concentration-dependent enhancement of FAS activity (Table 4).

The remarkable feature of the lowering of the serum cholesterol concentration mediated by feeding cholestrol inhibitor I is that only the LDL cholesterol fraction is lowered to a significant extent. This lowering in turn causes a significant lowering of serum total cholesterol. The temporal action of cholesterol inhibitor I on cholesterol metabolism suggests that first it is directed towards the inhibition of HMG Co-A reductase with a lowering of serum cholesterol level and substantially a substrate-mediated lowering of cholesterol 7-alpha-hydroxylase activity.

TABLE 1

EFFECT OF CHOLESTEROL INHIBITOR I ISOLATED FROM NONPOLAR FRACTION OF HPBF ON THE HEPATIC ENZYME ACTIVITIES AND ON SERUM LIPIDS IN 3-WEEK-OLD BROILER MALE CHICKENS.[1]

| Nutritional State | HMG-CoA Reductase[2] | Fatty Acid Synthetase[3] | Concentration in Serum (mg/100 ml) | | |
|---|---|---|---|---|---|
| | | | Total Cholesterol | HDL-Chol. | Chol-LDL |
| Corn (control) | 198 ± 15[a] (100)[4] | 168 ± 14[a] (100)[4] | 161 ± 13[a] (100)[4] | 54 ± 5[a] (100)[4] | 81 ± 7[a] (100)[4] |
| Corn + Chol. Inhib. I; 2.5 ppm | 172 ± 12[a,b] (87) | 190 ± 12[a] (118) | 152 ± 10[a] (94) | 54 ± 6[a] (100) | 73 ± 5[a] (90) |
| Corn + Chol. Inhib. I; 5.0 ppm | 161 ± 12[b] (81) | 202 ± 10[b] (120) | 144 ± 8[a] (89) | 51 ± 4[a] (94) | 60 ± 4[b] (74) |
| Corn + Chol. Inhib. I; 10.0 ppm | 144 ± 9[b,c] (73) | 210 ± 15[b,c] (125) | 125 ± 7[b] (78) | 52 ± 5[a] (96) | 54 ± 4[b] (67) |
| Corn + Chol. Inhib. I; 15.0 ppm | 135 ± 8[c] (68) | 218 ± 17[b,c] (130) | 122 ± 6[b] (76) | 50 ± 6[a] (93) | 52 ± 5[b] (64) |
| Corn + Chol. Inhib. I; 20.0 ppm | 130 ± 6[c] (66) | 235 ± 18[c] (140) | 105 ± 8[c] (65) | 48 ± 5[a] (89) | 38 ± 5[c] (47) |

[1] Feeding period was 3 weeks; Time of killing was 0800; Data expressed as mean ± SD; N = 9 chickens per group; HMG-CoA reductase = β-hydroxy-β-methyl-Glutaryl-Coenzyme A reductase.
[2] p-moles of mevalonic acid synthesized per minute per mg of microsomal protein.
[3] nmoles of NADPH oxidized per minute per mg of cytosolic protein.
[4] Percentage of respective control activity data are in parentheses.
[a-c] Values not sharing a common superscript letter are different at $P < 0.01$.

TABLE 2

EFFECT OF CORN BASED DIET SUPPLEMENTED WITH PETROLEUM ETHER SOLUBLE FRACTIONS (PESF) OF HIGH-PROTEIN BARLEY FLOUR (HPBF) AND ITS HPLC PURIFIED CHOLESTEROL INHIBITOR I ON BODY WEIGHTS, HEPATIC ENZYME ACTIVITIES AND SERUM CHOLESTEROL IN 3-WEEK OLD BROILER MALE CHICKENS

| Nutritional State | Body Weight | | Gain in Weight (gm) | HMG-CoA Reductase[3] | Fatty Acid Synthetase[4] | Serum Cholesterol (mg/dl) | | | Serum Triglycerides (mg/dl) |
|---|---|---|---|---|---|---|---|---|---|
| | Initial[1] | Final[2] | | | | Total-Chol. | HDL-Chol. | LDL-Chol. | |
| Corn | 47.8 ± 2[5] | 359 ± 49[5] | 311[5] | 198 ± 15[5,a] | 168 ± 20[5,a] | 161 ± 13[5,a] | 54 ± 5[5,a] | 81 ± 7[5,a] | 146 ± 6[5,a] |
| Corn + PESF of HPBF 20% equivalent to HPBF) | 48.3 ± 2 | 381 ± 46 | 333 | 142 ± 8[b] | 146 ± 14[b] | 111 ± 9[b] | 49 ± 4[a] | 55 ± 6[b] | 114 ± 5[b] |

TABLE 2-continued

EFFECT OF CORN BASED DIET SUPPLEMENTED WITH PETROLEUM ETHER SOLUBLE FRACTIONS (PESF) OF HIGH-PROTEIN BARLEY FLOUR (HPBF) AND ITS HPLC PURIFIED CHOLESTEROL INHIBITOR I ON BODY WEIGHTS, HEPATIC ENZYME ACTIVITIES AND SERUM CHOLESTEROL IN 3-WEEK OLD BROILER MALE CHICKENS

| Nutritional State | Body Weight Initial[1] | Body Weight Final[2] | Gain in Weight (gm) | HMG-CoA Reductase[3] | Fatty Acid Synthetase[4] | Serum Cholesterol (mg/dl) Total-Chol. | Serum Cholesterol (mg/dl) HDL-Chol. | Serum Cholesterol (mg/dl) LDL-Chol. | Serum Triglycerides (mg/dl) |
|---|---|---|---|---|---|---|---|---|---|
| Corn + Chol. Inh. I (5 ppm) | 48.3 ± 2 | 356 ± 33 | 308 | 134 ± 6[b] | 215 ± 18[c] | 105 ± 11[b] | 48 ± 5[a] | 38 ± 5[c] | 174 ± 6[c] |

[1]Weight of one-day-old broiler male chickens;
[2]Three-week-old broiler male chickens.
[3]pmoles of mevalonic synthesized per minute per mg of microsomal protein.
[4]nmoles of NADPH oxidized per minute per mg of cytosolic protein.
[5]Data expressed as mean ± SD; N = 9 chickens per group.
[a-c]Means within a column and without a commmon superscript are different at $p < 0.01$.

TABLE 3

EFFECT OF CHOLESTEROL INHIBITOR I ISOLATED FROM NONPOLAR FRACTION OF HPBF AND LEMON GRASS OIL ON THE HEPATIC ENZYME ACTIVITIES AND ON SERUM LIPIDS IN 13-WEEK-OLD WLH MALE CHICKENS.[1]

| Nutritional State | HMG-CoA Reductase[2] | Fatty Acid Synthetase[3] | Concentration in Serum (mg/100 ml) Total Cholesterol | HDL-Chol. | LDL-Chol. |
|---|---|---|---|---|---|
| Corn (control) | 484 ± 35[a] (100)[4] | 262 ± 7[a] (100)[4] | 129 ± 7[a] (100)[4] | 61 ± 3[a] (100)[4] | 67 ± 4[a] (100)[4] |
| Corn ± PESF of HPBF (20% equivalent to HPBF) | 372 ± 22[b] (77) | 240 ± 6[b] (92) | 119 ± 5[a] (92) | 60 ± 4[a] (98) | 56 ± 3[b] (84) |
| Corn + Chol. Inhib. 1 (20 ppm) | 305 ± 18[c] (63) | 292 ± 9[c] (111) | 103 ± 6[b] (80) | 58 ± 3[a] (95) | 44 ± 3[c] (66) |
| Corn + Lemon Grass Oil (20 ppm) | 347 ± 20[b] (72) | 360 ± 10[d] (137) | 112 ± 8[b] (87) | 65 ± 5[a] (107) | 50 ± 4[b] (75) |

[1]Feeding period was four weeks; Time of killing was 0800; Data expressed as mean ± SD; N = 8 chickens per group; HMG-CoA reductase = β-hydroxy-β-methylglutaryl Coenzyme A reductase.
[2]pmoles of mevalonic acid synthesized per minute per mg. of microsomal protein.
[3]nmoles of NADPH oxidized per minute per mg. of cytosolic protein.
[4]Percentage of respective control activity data are in parentheses.
[a-d]Values not sharing a common superscript letter are different at $P < 0.01$.

TABLE 4

EFFECT IN VITRO OF LEMON GRASS OIL AND CHOLESTEROL INHIBITOR I FROM HPBF OF DIFFERENT CONCENTRATIONS ON ACTIVITIES OF β-HYDROXY-β-METHYLGLUTARYL-COA REDUCTASE AND FATTY ACID SYNTHETASE IN ISOLATED HEPATOCYTES OF CHICKEN[1]

| A. Lemon Grass Oil | | | B. Cholesterol Inhibitor I from HPBF | | |
|---|---|---|---|---|---|
| Concentration (μg/ml)[2] | β-Hydroxy-β Methylglutaryl-CoA Reductase[3] | Fatty Acid Synthetase[4] | Concentration (μg/ml)[2] | β-Hydroxy-β Methylglutaryl-CoA Reductase[3] | Fatty Acid Synthetase[4] |
| 0 | 48 (100)[5] | 68 (100)[5] | 0 | 52 (100)[5] | 72 (100)[5] |
| 5 | 46 (96) | 80 (118) | 5 | 45 (87) | 88 (122) |
| 10 | 40 (83) | 104 (153) | 10 | 40 (77) | 97 (135) |
| 15 | 35 (73) | 107 (157) | 15 | 31 (60) | 112 (156) |
| 20 | 32 (67) | 128 (188) | 20 | 30 (57) | 126 (175) |
| 25 | 28 (58) | 157 (231) | 25 | 28 (54) | 135 (188) |
| 50 | 28 (60) | 123 (181) | 50 | 22 (42) | 148 (188) |
| 100 | 30 (63) | 126 (185) | 100 | 23 (44) | 154 (214) |

[1]Ten-week-old female chickens were fed standard corn-soy diet. They were fasted for 48 hrs. and refed 72 hrs. prior to the preparation of liver perfusion.
[2]Incubation period was 15 minutes. Values represent means of two replicates within incubation set.
[3]pmoles of mevalonic acid synthesized per minute per mg of microsomal fraction.
[4]nmoles of NADPH oxidized per minute per mg of cytosolic fraction.
[5]Percentage of respective control activity data are in parentheses. The results presented above were carried out by using the cells from one liver.

The active ingredients may be readily administered via the alimentary canal in the form of oral doses or by injection in sterile parenteral preparations.

Dosage forms of the compounds can be prepared by combining them with non-toxic pharmaceutically acceptable carriers as is well known in the art. Such carriers can be solid or liquid such as, for example, corn starch, lactose, sucrose, peanut oil, olive oil, sesame oil and water. If a solid carrier is used the dosage forms may be tablets, capsules, powders, troches or lozenges. If a liquid form is used, soft gelatin capsules, syrup or liquid suspensions, emulsions or solutions are convenient dosage forms. The dosage forms may also contain adjuvants such as preserving, stabilizing, melting or emulsifying agents, solution promoters, etc., and may or may not also include other therapeutically valuable substances.

The dosage ranges will commonly range from about 5.0 mg to 60 mg per day, but with the actual amounts being dependent upon, among other factors, patient condition and size, and the result to be achieved as well as other factors known to those skilled in the art in the therapeutic use of such medicinal agents.

The compositions of the present invention are useful as hypocholesterolemic agents and possess the additional advantage of not lowering the high density lipoprotein fraction of cholesterol (HDL-cholesterol), which is known to lower the risk factor of coronary heart disease (Gordon, T. et al., "High Density Lipoprotein as a Protective Factor Against Coronary Heart Disease," May 1977, *The American Journal of Medicine*, Vol. 62, pp. 707–714).

Although pure d-α-tocotrienol is preferred as the active ingredient for use in the compositions and method, lemon grass oil containing suitable concentrations of the active ingredient may also be used, e.g., in the form of capsules or emulsions. In addition, pharmaceutically acceptable derivatives of the d-α-tocotrienol may be preferred for use in some compositions and are intended to be within the scope of the invention.

The foregoing description has been for purposes of illustration. The invention is not intended to be limited except by the claims which follow.

We claim:

1. The method of lowering blood cholesterol levels in an animal in need of a lowered cholesterol which comprises administering to said animal a safe and effective amount of a compound of the following formula:

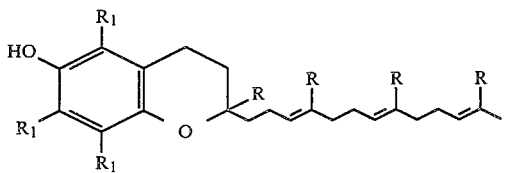

in which R and $R_1$ are lower alkyls of 1 to 4 carbon atoms.

2. The method of claim 1 in which the compound is d-α-tocotrienol.

3. A method of lowering total cholesterol levels and low density lipoprotein levels in the blood of an animal in need of a lowered cholesterol and low density lipoprotein levels which comprises administering to said animal a safe and effective amount of a compound of the following formula:

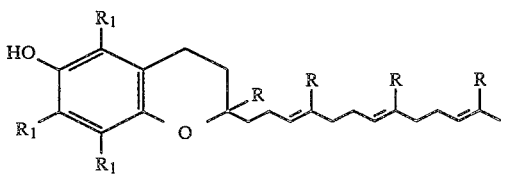

in which R and $R_1$ are lower alkyls of 1 to 4 carbon atoms.

4. A method of claim 3 in which the compound is d-α-tocotrienol.

* * * * *